Sept. 10, 1963 G. J. VON ABRAMS Plant Pat. 2,280
ROSE PLANT
Filed Dec. 17, 1962
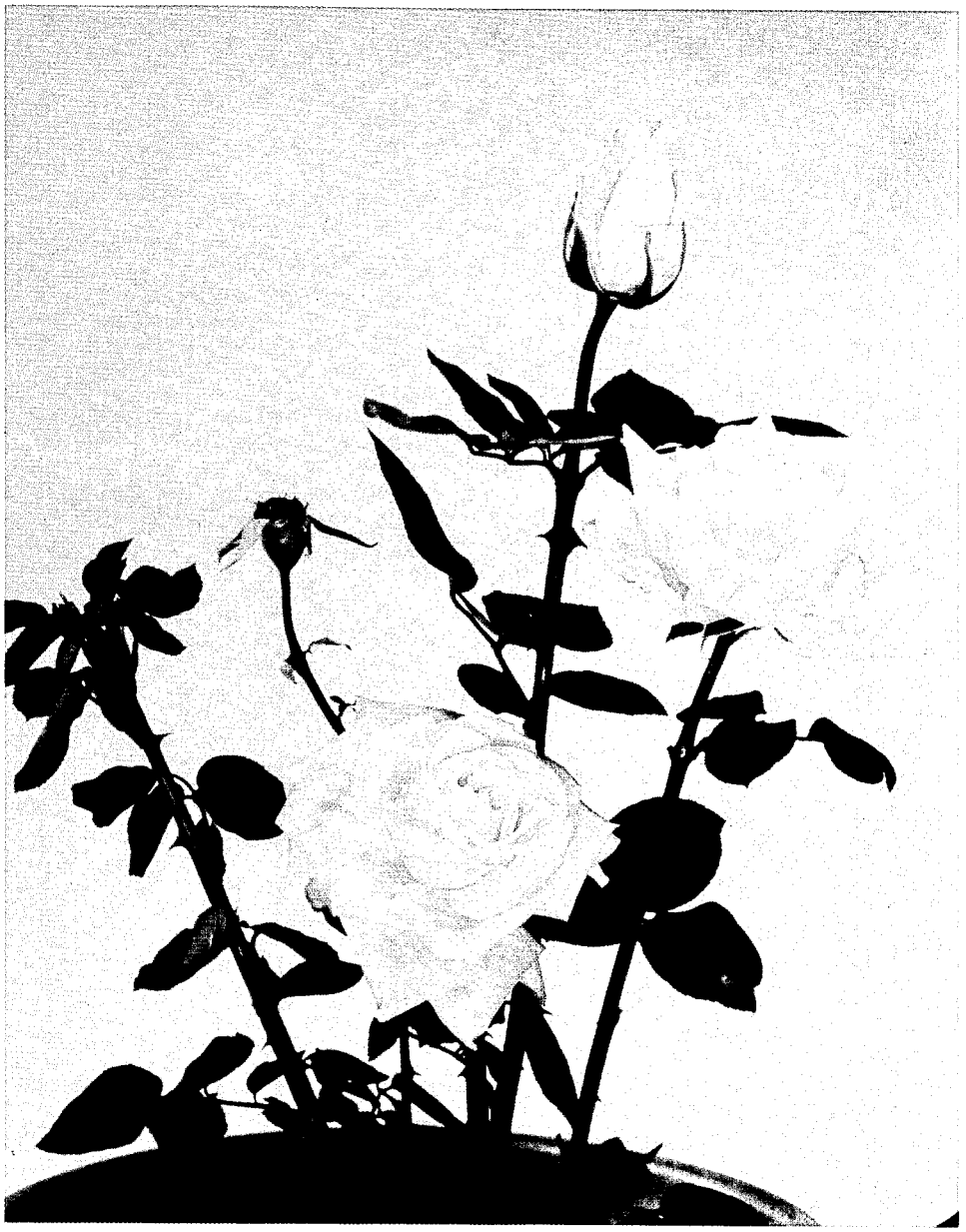
INVENTOR.
GORDON J. VON ABRAMS
BY F. R. Geisler.
ATTORNEY United States Patent Office Plant Pat. 2,280
Patented Sept. 10, 1963

2,280
ROSE PLANT

Gordon J. Von Abrams, 3463 NW. Savier St., Portland, Oreg.

Filed Dec. 17, 1962, Ser. No. 267,876
1 Claim. (Cl. Plt.—11)

This invention comprises a new and distinct variety of rose plant of the commercial "hybrid tea" class which was obtained by pollinating the rose variety "PD 49271–3" (not in commerce), which had been obtained by crossing the rose variety "Blanch Mallerin" (Plant Patent No. 594), with the rose variety "Peace" (Plant Patent No. 591), with pollen of the rose variety "P.D. 49510–1" (not in commerce), which had been obtained by crossing the rose variety "Peace" (Plant Patent No. 591) with the well known rose variety "Frau Karl Druschki."

The pollination took place at Scappoose, Oregon in the spring of 1951, the seed was planted in the fall of 1951, the first asexual propagation was performed in 1953 at Scappoose, Oregon, by bud-grafting.

The objective of this particular breeding was mainly to produce a rose variety which would have a large, many-petaled, elegantly formed flower in the white or near-white color range, and this objective was achieved.

The main distinguishing features of this new rose variety are the long tapered bud, the excellent symmetry of the large flower, and the color range of from white to pale pink, the texture of the petals adding to the color effect. This new variety is clearly distinct from its parent varieties (which are not in commerce), the plant and foliage being smaller than either parent variety, the flower being larger than that of the seed parent but smaller than that of the pollen parent, and being more nearly white than the flower of either parent variety. This new plant has been shown to retain its distinguishing characteristics through successive propagations, by bud-grafting.

Of the rose varieties in commerce, the new variety may be best compared to the rose variety "Dresden" (Plant Patent No. 1,857), but the new variety has, in general, fewer petals, longer and more tapered buds, more regular flower form, petals of heavier substance, a more pink flower color in late season and many more stamens than "Dresden." The new variety also tends to larger thorns and more "corkiness" of the older branches.

This new variety is a medium tall bush type of plant, suitable for outdoor use, and desirable for cut flowers and for garden decoration.

The accompanying illustration shows the vegetative growth and the flowers of the rose plant in different stages of development, and shows the color, as nearly as is resonably possible in a color illustration of this type. The illustration was made in September 1960, from a plant grown at Scappoose, Oregon.

A more detailed description follws in which the following color references are used:

(1) Wilson, R. F.: Royal Horticultural Society Colour Chart, England, 1940. (Hereafter abbreviated "W.")

(2) Ridgway, R.; Color Standards and Color Nomenclature, Washington, D.C., 1912. (Hereafter abbreviated "R.")

FLOWERS

*Open Flowers*

The flowers are borne from one to four or five per stem on strong, long stems. The plant blooms abundantly outdoors and blooms nearly continuously during the growing season.

The open flower is large in size, averaging up to about 5½ inches across. Petalage—double—32 to 60 depending upon environment. The flower form is high-centered throughout development, with excellent symmetry. The petals roll outward at the apex, giving the appearance of a lip around a central orifice. The flowers have a moderate fragrance. The general color effect of the newly open flower is near-white, deepening to rose pink (W. 427/1, p. 126) towards the center. Then subsequently the flower becomes somewhat paler and more nearly white, the general color effect being white. The fading progresses from the outer petals towards the center of the flower.

*Flower Petals*

Substance: Medium thick, soft, flexible.
Texture: Outside shiny; inside satiny.
Shape and size (in open flower):
- *Outside petal.*—Obovate, near orbicular, i.e. 6 cm. x 6 cm. Apex entire.
- *Inside petal.*—Broadly obovate, sometimes with apical irregularity.

*Petal Color*

The following description of a newly open flower was made in July 1960, from specimens, grown outdoors near Scappoose, Oregon.

Outside petal:
- *Outer surface.*—Basal fan near Dresden Yellow (W. 64/3, p. 64). Near-white above, flushed pale pink near Rose Pink (W. 427/3, p. 126) towards margins.
- *Inner surface.*—Basal fan near Dresden Yellow (W. 64/2, p. 64). Near-white above, flushed near Rose Pink (W. 427/3, p. 126) toward margins.

Intermediate petal:
- *Outer surface.*—As outside petal, slightly darker at apical lateral margins, near W. 427/2.
- *Inner surface.*—As outside petal, but slightly greater area flushed pink. Darker pink at margins, near W. 427/2.

Inside petal:
- *Outer surface.*—Basal fan near Dresden Yellow (W. 64/2, p. 64). Pink above, near Rose Pink (W. 427/1, p. 126).
- *Inner surface.*—Basal fan near Dresden Yellow (W. 64/1, p. 64). Near-white above, flushed near Rose Pink (W. 427/1, p. 126) toward margins.

*Behavior of Flower in Senescence*

Petals drop cleanly after continued fading to white or near white. Under conditions of low light intensity and/or low temperature, the flower develops less of the pink coloration, opening near white. Also, at very high temperatures, there is less pink pigmentation, fading occurs more rapidly, and the petals may appear burned at the outer margins. Flower longevity: greater than average.

BUD

Peduncle:
- *Size.*—Medium (i.e., 4 mm. x 5 cm.).
- *Strength.*—Erect.
- *Color.*—Near Scheele's Green (W. 860/2, p. 175), variably flushed reddish.
- *Surface.*—Smooth, few gland-tipped cilia.

Sepals:
- *Size.*—Medium (i.e., 1 x 3 cm.).
- *Form.*—Spear-shaped.
- *Point.*—Long, acuminate, seldom bristled.
- *Lateral margins.*—Several gland-tipped cilia; few slender bristle-like appendages.
- *Surface.*—Outer surface—rugose, with slight gloss. Inner surface—tomentose.
- *Color.*— Outer surface—between Scheele's Green (R. 33. GY-G. *i*. Plate VI) and Grass Green (R. 33. GY-G. *k*, Plate VI). Inner surface—near Corydalis Green (R. 29'''. GG-Y. *d*, Plate XLI).

*Behavior.*—Reflex.

Before calyx breaks:

*Size.*—Large.

*Form.*—Long pointed, with medium terminal appendages.

*Color.*—Near Scheele's Green (R. 33. GY-G. *i*, Plate VI).

As calyx breaks: Petal color exposed near Chrysanthemum Crimson (W. 824/3, p. 169).

As first petal opens:

*Size of bud.*—Large.

*Form of bud.*—Long-pointed.

*Color of petal.*—Outer surface—basal fan near Light Green-Yellow (R. 27. G-Y, *d*, Plate V) fading shortly above, to near white, blending to Neyron Rose (W. 623/1, p. 76) or, toward the margins (W. 623, p. 76). Inner surface—as outer surface, except that the near-white area is larger, and near-white is the predominant color.

Opening habit: Opens well under most weather conditions.

REPRODUCTIVE ORGANS

Stamens:

*Quantity.*—Moderate.

*Position.*—Immediately inside corolla.

*Filaments.*—Moderate length (i.e., 11 mm.); pale yellow.

*Anthers.*—Size ordinary; color light orange.

*Pollen.*—Normal.

Pistils:

*Quantity.*—Moderate.

*Styles.*—Long (i.e., 15 mm. above disc); free, but base enclosed in mass of cottony tissue rising well above disc; contortion normal.

*Stigmas.*—Ordinary; grayish color, small.

*Ovaries.*—Several to many exposed above receptacle, but surrounded by dense cottony tissue.

Receptacle and calyx-tube:

*Size.*—Small.

*Shape.*—Obovate to near turbinate.

*Surface.*—Smooth.

*Color.*—Near, but somewhat grayer than Scheele's Green (R. 33. GY-G. *i*, Plate VI).

Seed pod:

*Size.*—Medium (i.e., 2 x 2.5 cm.).

*Shape.*—Obovate, with many seeds exposed.

*Sepals.*—Generally persistent.

*Surface.*—Smooth; with several small corky areas.

*Wall.*—Medium thick, fleshy.

*Color at maturity.*—Variable orange.

Seeds: Numerous, large, viable.

PLANT

Foliage:

*Leaves.*—Compound, 5 to 7 leaflets; normally abundant.

*Leaflets.*—Substance—medium thick; hard, flexible. Texture—smooth; medium gloss. Size—medium (i.e., terminal leaflet 5 x 7 cm.). Shape—broadly ovate; apex acuminate; base slightly cordate; margin serrate. Color: mature—upper surface— darker than Spinach Green (W. 0960, p. 187); under surface—near Pois Green (R. 29'''. GG-Y. *i*, Plate XLI); young—upper surface—near Spinach Green (W. 0960/1, p. 187); heavily flushed near Victoria Lake (R. 1. RED. *m*, Plate I) especially along veins and margins; under surface—near Victoria Lake (R. 1. RED. *m*, Plate I), or lighter variably flushed green.

Rachis:

*Caliber.*—Medium heavy.

*Upper side.*—Ordinary, lateral ridges with several gland-tipped cilia.

*Under side.*—With few small thorns; several short gland-tipped cilia.

Stipules:

*Size.*—Medium large (i.e., 22 x 8 mm.).

*Points.*—Medium (i.e., 5 mm.); nearly straight; angle near 45°.

*Margins.*—Heavily glandular.

Disease resistance: Ordinary for class.

Growth:

*Habit.*—Medium tall; full, moderately branched; upright.

*Vigor.*—Moderate.

*Canes* (*in 2nd year of growth*).—Caliber—medium (i.e., 9 cm.). Surface—somewhat corky, w/several medium thorns. Color—grayish brown, often mottled green.

*Main stems* (*of current year's growth*).—Caliber—medium (i.e., 1 cm.). Surface—smooth, slightly glaucous; thorns—large—several; size (i.e., 11 mm.); hooked slightly downward; color near Hessian Brown (R. 5'. 00-R. *m*, Plate XIII); base long oval (i.e., 4 x 16 mm.); small—none; cilia—none. Color—near Cress Green (R.29''. GG-Y. *k*, Plate XXXI).

*Branches* (*currently bearing fruit or senescent flowers*).—Caliber—heavy (i.e., 5 mm. at first internode below flower). Surface—smooth, slightly glaucous; thorns—several, small (i.e., 7 mm.); hooked strongly downward; color near Hessian Brown (R-5'. 00-R. *m*, Plate XIII); base oval (i.e., 3 x 8 mm.). Color—near Chromium Green (R. 31''. Y-G. *i*, Plate XXXII); sometimes lightly mottled reddish-brown.

*New shoots* (*in rapid growth*).—Surface—smooth; thorns—several; medium (i.e., 6 mm.); hooked strongly downward; color near Ox Blood Red (R. 1. RED. *k*, Plate I); base oval (i.e., 1.5 x 5 mm.). cilia—none. Color—near Oil Green (R. 27. G-Y, *k*, Plate V), almost completely over-flushed near Prussian Red (R. 5''. CO-R. *k*, Plate XXVII).

Durability and low-temperature tolerance of plant: Ordinary.

Having thus disclosed my invention, I claim:

A new an distinct variety of rose plant of the "hybrid-tea" class, substantially as herein described and shown, bearing flowers in the white or near-white color range, and characterized particularly by the excellent symmetry of the large, many-petaled flowers and the texture and coloring of the petals.

No references cited.